(12) United States Patent
Sharp

(10) Patent No.: US 6,699,223 B2
(45) Date of Patent: Mar. 2, 2004

(54) SAFETY SYRINGE WITH RELEASABLE ANTI-ROTATION RETRACTABLE NEEDLE ADAPTER

(75) Inventor: Fraser R. Sharp, Vancouver (CA)

(73) Assignee: Invrio Medical Devices Ltd., Bridgetown (BB)

( * ) Notice: Subject to any disclaimer, the term of this patent is extended or adjusted under 35 U.S.C. 154(b) by 410 days.

(21) Appl. No.: 09/842,318

(22) Filed: Apr. 26, 2001

(65) Prior Publication Data

US 2002/0161340 A1 Oct. 31, 2002

(51) Int. Cl.⁷ .................................. A61M 5/32
(52) U.S. Cl. ........................ 604/195; 604/181
(58) Field of Search .................. 604/195, 110, 604/187, 192, 218, 228, 240–243, 263

(56) References Cited

U.S. PATENT DOCUMENTS

| 5,205,823 A | 4/1993 | Zdeb |
| 5,273,543 A | 12/1993 | Bell et al. |
| 5,401,246 A | 3/1995 | Mazur et al. |
| 5,997,511 A | * 12/1999 | Curie et al. ............. 604/195 |
| 6,117,113 A | 9/2000 | Novacek et al. |

FOREIGN PATENT DOCUMENTS

WO    WO/ 92/11883    7/1992

* cited by examiner

*Primary Examiner*—Manuel Mendez
(74) *Attorney, Agent, or Firm*—Nixon & Vanderhye

(57) ABSTRACT

The syringe includes an adapter threaded into the distal end of the barrel and a plunger axially movable within the barrel. A stop and catch cooperate between the adapter and barrel end to prevent rotation of the adapter. Adapter and plunger engagement structures are carried by the plunger and adapter, respectively, to enable joint rotation of the plunger and adapter relative to the barrel to unthread the adapter from the barrel end and withdraw the adapter and needle carried thereby jointly with the plunger into the interior of the barrel. The engagement structures also include an element for engaging the catch in response to axial movement of the plunger to release the adapter for rotational movement relative to the barrel end and subsequent withdrawal of the adapter and needle carried thereby into the barrel.

23 Claims, 8 Drawing Sheets

SAFETY SYRINGE WITH RELEASABLE ANTI-ROTATION RETRACTABLE NEEDLE ADAPTER

TECHNICAL FIELD

The present invention relates to a safety syringe for medical and industrial applications and particularly relates to a syringe having a needle adapted for withdrawal into the barrel of the syringe after use for disposal purposes, thereby eliminating or minimizing needlestick injuries.

BACKGROUND

Needlestick injuries from syringe needles are a common and increasing problem and cause significant concern because of the potential for transmission of diseases such as AIDS and Hepatitis B. A discussion of this type of injury and a variety of solutions to avoid the injury by using a syringe having a retractable needle are discussed in U.S. Pat. No. 6,117,113, of common assignee herewith, the disclosure of which is incorporated herein by reference. Various mechanical structures are disclosed in that patent and other patents for withdrawing a needle into the barrel of the syringe after use. A number of such structures rely on an interaction between an adapter carrying the needle, the distal end of the barrel and the axially movable plunger to withdraw the needle into the syringe barrel. Particularly, in a form of syringe preferred by assignee of the present application, the adapter is releasable from the distal end of the barrel by engaging the plunger with the adapter and rotating the adapter relative to the barrel. This enables the adapter, together with the needle carried thereby, to be released from the barrel end and withdrawn into the syringe barrel as the plunger is axially withdrawn in a direction away from the distal end of the barrel. The adapter is preferably screw threaded into the barrel end, although the rotational action to release the adapter is not limited to a screw thread, e.g., a bayonet-type joint could be used.

While screw threads once torqued have substantial resistance to rotation in a direction tending to release the adapter from the barrel end, there remains the potential for inadvertent rotation of the adapter in a direction relative to the barrel end which would release the adapter from the barrel end. For example, this may occur during application of a standard Luer needle onto a Luer locking element on the adapter or barrel end. It will also be appreciated that inadvertent rotation of the adapter relative to the barrel in a direction tending to release the adapter from the barrel breaks the seal between the adapter and barrel. Accordingly, there is a need to preclude inadvertent rotation of the adapter relative to the barrel in a direction tending to release or unseal the adapter from the barrel end, while simultaneously enabling the adapter to be rotated in the same direction to intentionally release the adapter from the barrel for withdrawal with the needle into the barrel.

DISCLOSURE OF THE INVENTION

In accordance with a preferred embodiment of the present invention, there is provided a safety syringe having an adapter for carrying a needle and which adapter is rotationally releasable from the distal end of the barrel to enable withdrawal of the adapter, including the needle carried thereby, into the syringe barrel while precluding inadvertent rotation of the adapter relative to the barrel in the same direction to release or unseal the adapter from the barrel end. As described in the above-identified patent, the plunger carries adapter engagement structure at its distal end, while the adapter carries plunger engagement structure at its proximal end. Upon engagement of the plunger with the adapter, the plunger is rotationally self-aligned relative to the barrel and adapter, enabling drive surfaces on the adapter engagement structure of the plunger to engage driven surfaces on the plunger engagement structure of the adapter whereby the adapter can be rotationally released from the distal end of the barrel in response to joint rotation of the plunger and adapter relative to the barrel. In accordance with the present invention, however, the adapter and distal end of the barrel have interengaging elements which inhibit or preclude rotation of the adapter relative to the distal end of the barrel in a direction tending to release the adapter from the barrel end. Additionally, the engagement structures between the plunger and adapter cooperate to disable the interengaging elements and release the adapter for rotation relative to the barrel, thus enabling the adapter to be rotated relative to and to be released from the barrel end and, together with the needle, withdrawn into the barrel.

The interengaging elements between the adapter and the barrel end particularly include one or more stops carried by one of the adapter and barrel end and one or more catches carried by the other of the adapter and barrel end. In a preferred embodiment, the barrel has a plurality of circumferentially spaced splines and the adapter includes one or more catches engageable with the splines to prevent or inhibit rotation of the adapter relative to the barrel in a direction tending to release or unseal the adapter from the barrel end.

More particularly, each catch, preferably carried by the adapter, comprises a finger elastically flexible in a generally radial direction for engaging a spline on the barrel end. By engaging the spline, rotation of the adapter relative to the barrel end in a direction to release or unseal the adapter from the barrel end is precluded. To release the adapter for rotational movement relative to the barrel end, the adapter-engagement structure carried by the distal end of the plunger has surfaces which, in response to axial movement of the plunger toward the distal end of the barrel, cooperate with the fingers to displace the fingers, e.g., in a radially inward direction, from engagement with the stops. Preferably, the plunger includes a generally annular element which contacts tapered surfaces on the fingers to displace the fingers radially inwardly to release the adapter for rotation relative to the barrel end. Additionally, the element includes a radially projecting rib which engages in a radially outwardly opening slot of each finger to connect the plunger and adapter to one another. The rib and each finger and slot are configured to permit the fingers to be displaced radially inwardly from a first position preventing rotation between the barrel and the adapter, hence locking the adapter to the barrel end, into a second position. In that second position, the catches on the fingers clear the splines by a substantial margin. The rib and fingers then cooperate to permit displacement of the fingers radially outwardly into a third position in which the rib maintains the catches clear of the splines. Also, in that third position with the ribs engaging in the slots of the fingers, the adapter and plunger are connected one to the other for joint axial movement. Consequently, after the interengaging elements are disabled and upon joint rotation of the plunger and adapter relative to the barrel, the adapter is rotated into a position releasing it from the barrel end thereby, enabling the adapter and needle carried thereby to be withdrawn into the barrel upon joint axial withdrawing movement of the plunger and adapter.

In a preferred embodiment according to the present invention, there is provided a syringe comprising an axially elongated barrel having a hollow interior, an adapter carried by the barrel adjacent a distal end thereof and releasable therefrom in response to rotation relative to and about the axis of the barrel, the adapter having a passage for providing fluid communication with the interior of the barrel, a plunger axially movable in the barrel between positions axially spaced from the adapter and engaging the adapter, adapter-engagement structure disposed adjacent a first end of the plunger and engageable with plunger engagement structure on the adapter for enabling rotation of the adapter relative to the barrel in response to relative rotation of the plunger and barrel to cause the adapter to part from the distal end of the barrel, the structures having engageable surfaces enabling withdrawal of the adapter, when parted from the distal end of the barrel, into the interior of the barrel upon joint axial movement of the plunger and the adapter in a direction away from the distal end of the barrel and a stop carried by one of the adapter and the distal end of the barrel and a catch carried by another of the adapter and the distal end of the barrel engageable with the stop in a first position thereof to at least inhibit relative rotational movement of the adapter and the distal end of the barrel in a direction tending to cause the adapter to part from the distal end of the barrel, the catch being movable to a second position to release the adapter and the distal end of the barrel for relative rotational movement enabling the adapter to part from the distal end of the barrel in response to relative rotation of the adapter and the barrel.

In a further preferred embodiment according to the present invention, there is provided a syringe comprising an axially elongated barrel having a hollow interior, an adapter carried by the barrel adjacent a distal end thereof and removable therefrom in response to rotation relative to and about the axis of the barrel, the adapter having a passage for providing fluid communication with the interior of the barrel, a plunger axially movable in the barrel between positions axially spaced from the adapter and engaging the adapter, an adapter-engagement structure disposed adjacent a first end of the plunger and engageable with mating engagement structure on the adapter for enabling rotation of the adapter and distal end of the barrel relative to one another to cause the adapter to part from the distal end of the barrel, means cooperable between the adapter and the barrel for preventing relative rotation of the adapter and the distal end of the barrel, connective surfaces engageable between the plunger and adapter enabling withdrawal of the adapter, when parted from the distal end of the barrel, into the interior of the barrel upon joint axial movement of the plunger and the adapter in a direction away from the distal end of the barrel and means cooperable between the plunger and the adapter for disabling the preventing means thereby enabling relative rotation of the adapter and the distal end of the barrel and withdrawal of the adapter, when parted from the distal end of the barrel, into the interior of the barrel.

BEST MODE FOR CARRYING OUT THE INVENTION

Figure 1:
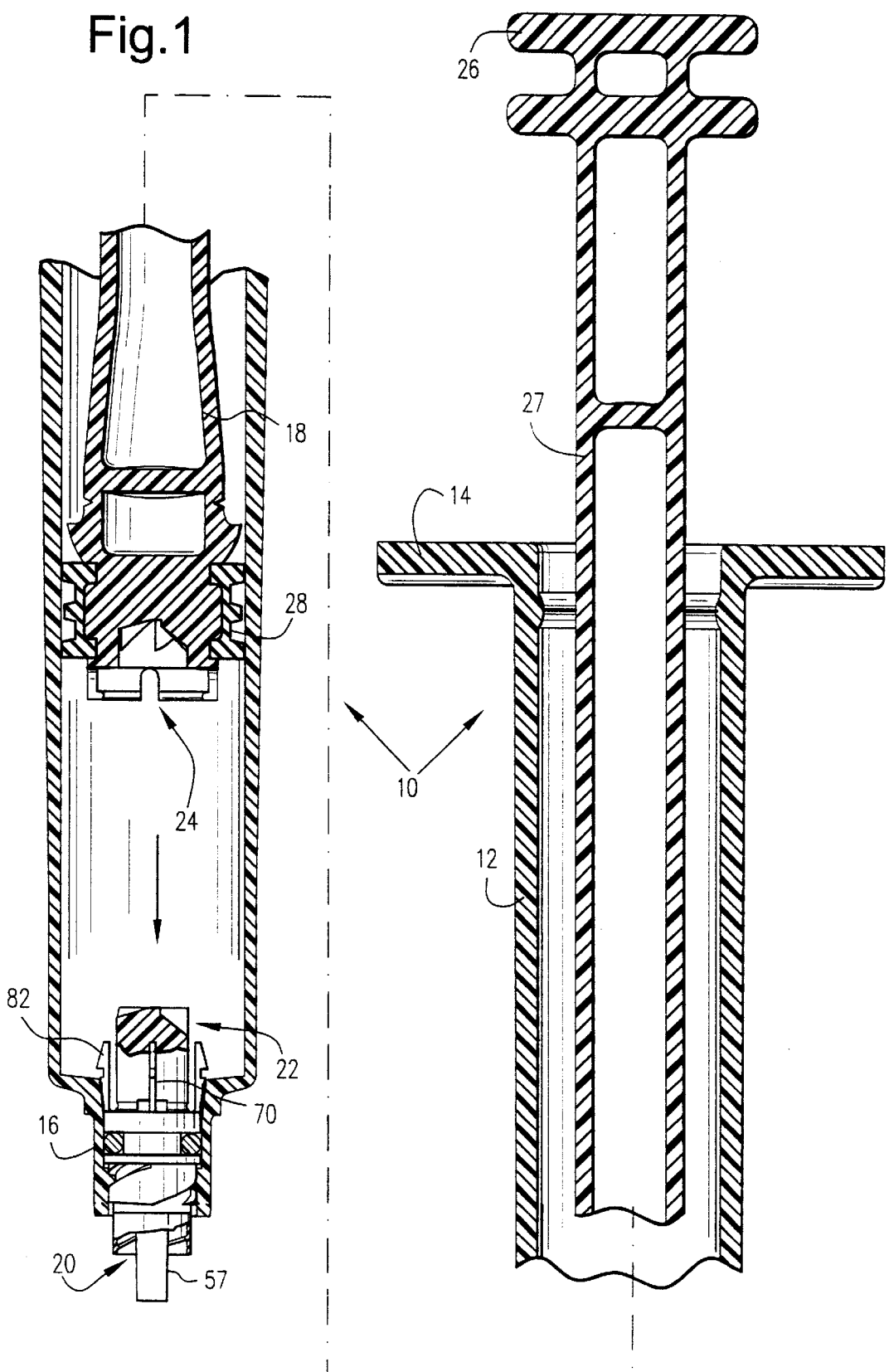
FIG. 1 is an exploded cross-sectional view with parts broken out of a syringe constructed in accordance with a preferred embodiment of the present invention and illustrating the adapter releasably secured to the distal end of the syringe barrel.

Referring now to the drawings, particularly to FIG. 1, there is illustrated a syringe, generally designated 10, comprised of an elongated, generally cylindrical barrel 12 having finger flanges 14 at a proximal end, a reduced diameter distal end 16, and a plunger 18. An adapter, generally designated 20, is releasably secured to the distal end 16 of the barrel 12. The adapter 20 includes plunger-engagement structure, generally designated 22, for engaging adapter-engagement structure, generally designated 24, carried on the distal end of plunger 18. The plunger 18, as illustrated in FIG. 1, terminates at its proximal end in a finger press 26.

Figure 2:
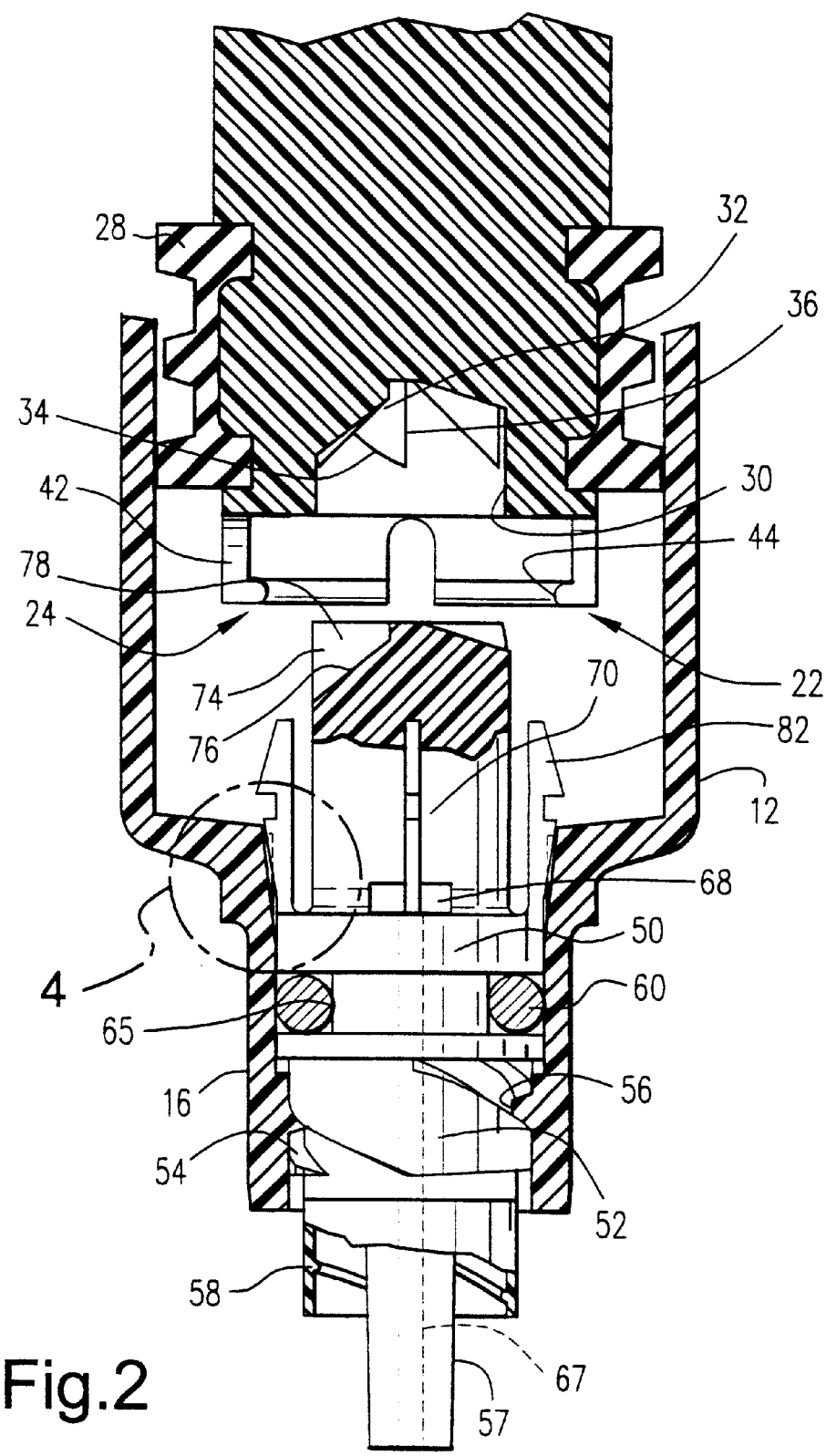
FIG. 2 is an enlarged fragmentary cross-sectional view illustrating the adapter and distal ends of the barrel and plunger with the plunger poised to unlock the adapter from the barrel end and connect with the adapter for joint rotational and axial movement.
Figure 4:
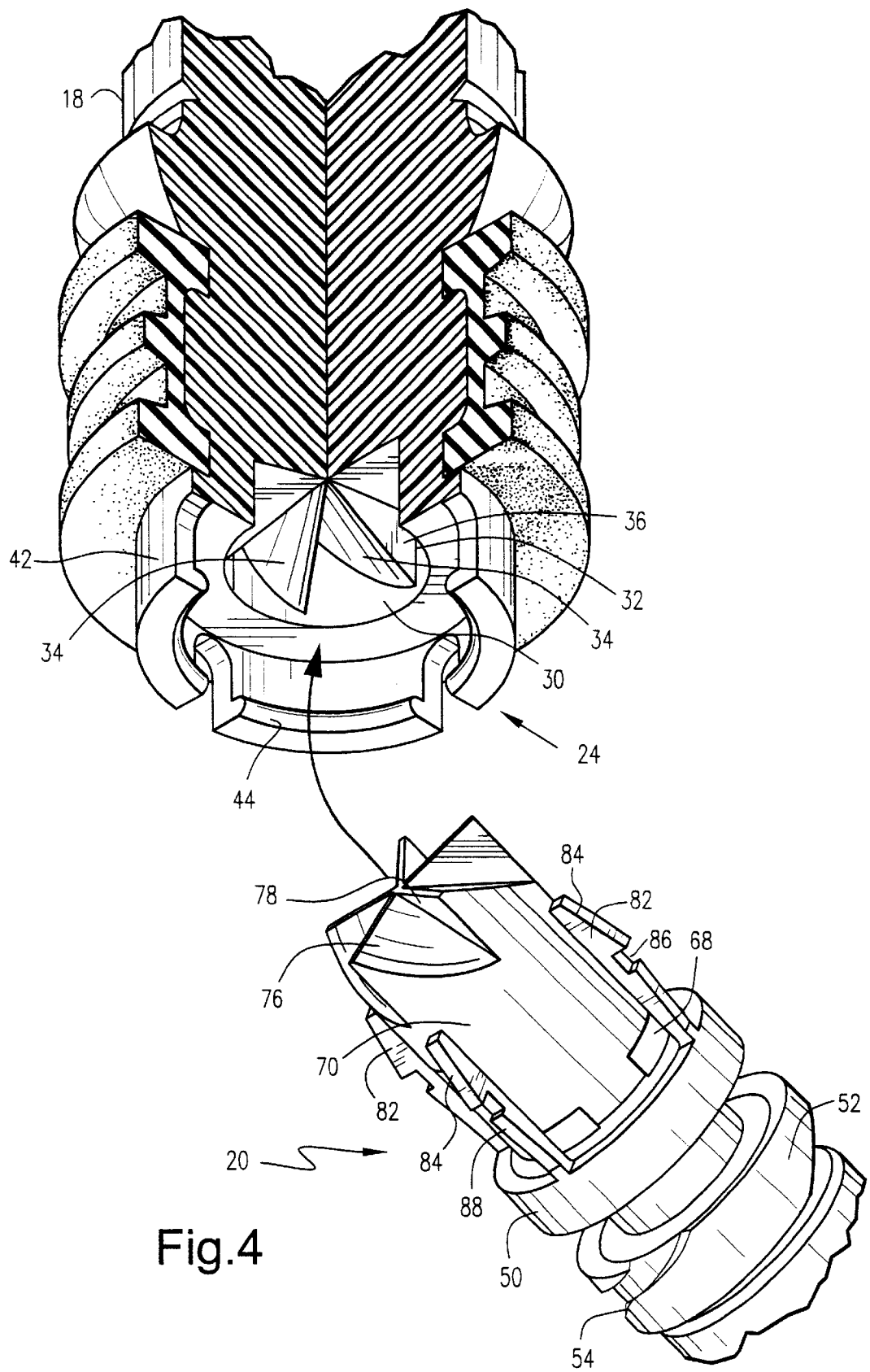
FIG. 4 is a fragmentary perspective view of adjoining ends of the plunger and adapter with parts in cross-section for clarity.

The plunger 18 has a plunger body 27, which may take various forms in cross-section, for example, cruciform, cylindrical, U-shaped or otherwise, terminating at its proximal end in finger press 26 and mounting adjacent its distal end a bung 28 for sealing engagement against the interior walls of the barrel 12. As best illustrated in FIGS. 2 and 4, the adapter-engagement structure 24 at the distal end of the plunger 18 includes a generally cylindrical female recess 30 having arcuate, radially inwardly extending projections or teeth 32 having circumferentially spaced alignment surfaces 34 and drive surfaces 36. Thus, the teeth 32 are circumferentially spaced from one another and each tooth has a tapered, circumferentially extending alignment surface 34 and an axially and radially inwardly extending drive surface 36.

A generally annular rim 42 projects from the distal end of plunger 18 and terminates in a radially inwardly extending, generally annular interrupted lip or rib 44. The rib 44 and the alignment and drive surfaces 34 and 36, respectively, form the adapter-engagement structure 24 on the distal end of the plunger 18.

The adapter 20, as best illustrated in FIGS. 2 and 4, includes a generally cylindrical adapter body 50 having an intermediate section 52 with male threads 54 for engaging corresponding female threads 56 (FIG. 2) formed in the reduced diameter section 16 of barrel 12. Adapter 20 terminates in a frustoconical section 57 (FIG. 2) to which a standard needle 59 (FIG. 6) may be attached by friction or by a conventional Luer lock having a needle hub 61 with flanges 63 engageable with a thin-walled, internally threaded section 58 on the distal end of the adapter. Alternatively, the adapter 20 may mount a needle integrally with the adapter, for example, by receiving a portion of the needle within a central axial opening and adhesively securing the needle and the adapter to one another. The central cylindrical body 50 of the adapter 20 includes an annular recess 65 for retaining an O-ring seal 60 for bearing against the internal reduced diameter section 16 of the barrel 12. The adapter 20 includes a central axial passage 67 (FIG. 2)

opening through its distal end and extending to an intermediate location where the passage turns to form two or more radially extending passages 68 opening radially of the adapter body 50. Consequently, a fluid passage lies in communication between the interior of barrel 12 and through the needle via the openings 68 and the axial passage 67 through the adapter for expressing fluid from or receiving fluid into the barrel.

The proximal end of the adapter 20, as best illustrated in FIGS. 2 and 4, has a reduced diameter body portion or male projection 70 terminating at a proximal end in a portion of the plunger engagement structure 22 generally complementary in shape to a corresponding portion of the adapter-engagement structure 24 carried by the distal end of the plunger. Thus, the cylindrical male projection 70 terminates in circumferentially spaced teeth 74 which project both axially and radially. Each tooth 74 has alignment and drive surfaces 76 and 78, respectively.

Figure 3:
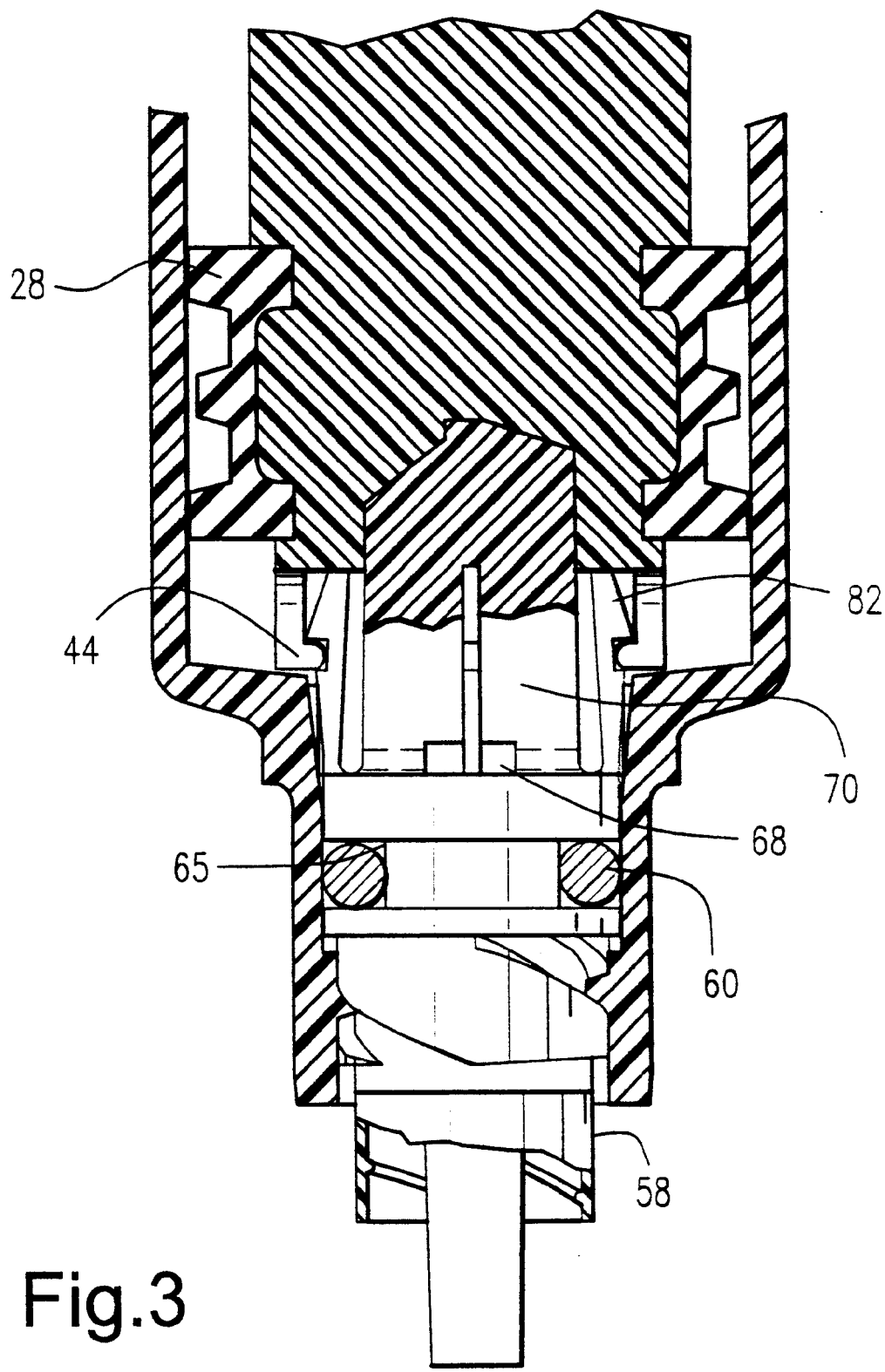
FIG. 3 is a view similar to FIG. 2 illustrating the plunger connected to the adapter and the interengaging elements disabled from locking the adapter and barrel to one another.
Figure 5A:
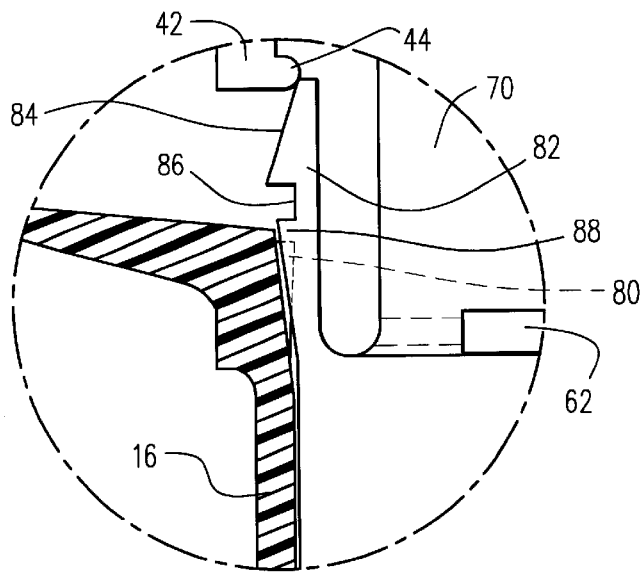
FIGS. 5A—5C are enlarged fragmentary cross-sectional views illustrating in sequence the release of the adapter for rotation relative to the barrel end and the connection of the plunger and adapter to one another according to an embodiment of the present invention.

As noted previously, the adapter and the barrel end are inhibited or prevented from rotation relative to one another to preclude inadvertent relative rotation therebetween in a direction tending to release and/or unseal the adapter relative to the barrel end. To accomplish this, the engagement of the adapter and barrel end includes an anti-rotation feature. As best illustrated in FIGS. 3 and 5A, this feature includes a plurality of circumferentially spaced splines 80 about an enlarged interior diameter end of the barrel 12 tapered in a direction away from the distal end of the barrel. The splines thus extend axially and project radially inwardly. The adapter mounts two or more, and preferably four, fingers 82 spaced circumferentially equidistantly from one another and radially outwardly of the reduced diameter body portion 70 of the adapter. The fingers 82 also project in an axial direction from the central cylindrical body 50 toward the plunger. The fingers 82 are elastically flexible in a radially inward direction toward body portion 70. Each finger 82 includes an outer surface 84 tapering toward the axis of the syringe in a direction toward the plunger, terminating in a recess or slot 86 below the tapered portion 84. A radial projection 88 on each finger below slot 86 extends a distance in a radial outward direction to lie radially outwardly of the radial inward confines of the splines 80.

With the fingers in the position illustrated in FIG. 5A, the fingers 82 serve as catches and inhibit or prevent rotation of the adapter 20 in a direction tending to unseal or release, e.g., unscrew the adapter from the barrel end. It will be appreciated that side surfaces of the splines 80 may be tapered to permit the fingers to ratchet past the splines when the adapter is rotated to connect it to the barrel, e.g., screw threaded into the barrel and torqued to retain the adapter in the barrel. Thus, the projections 88 and the splines 80 comprise interengaging elements, e.g., catches-and-stops, respectively, preventing or inhibiting relative rotation of the adapter and barrel end in a direction tending to release the adapter from the barrel end. It will be appreciated, however, that the adapter 20 must be rotated in a direction for release from the barrel end, e.g., the adapter must be unscrewed from the barrel end, before the adapter and the needle carried thereby can be withdrawn from the barrel end and into the barrel. Hence, the interengaging elements must be disabled before the adapter and needle carried thereby can be withdrawn into the barrel.

Figure 5B:
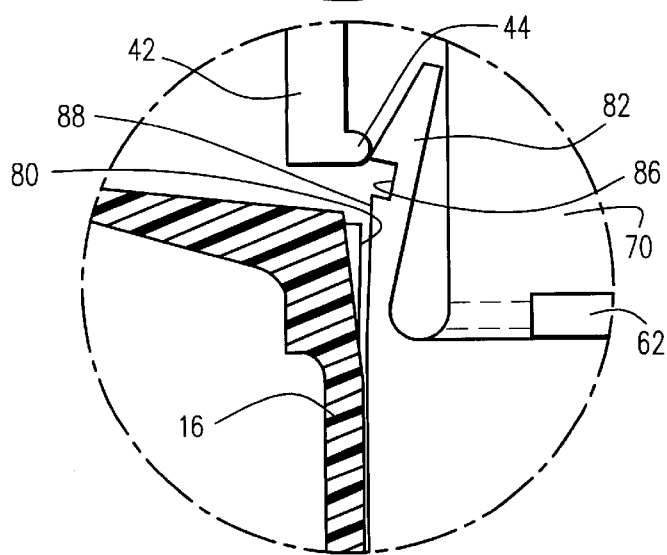

To accomplish the foregoing, the adapter-engagement structure 24 and the plunger-engagement structure 22 are configured to disable the interengaging elements, e.g., release the fingers 82 from their engagement with the splines 80. This is preferably accomplished upon axial movement of the plunger toward the distal end of the barrel substantially simultaneously as the respective adapter-engagement structures engage one another to align the plunger and adapter so that the plunger and adapter can be jointly rotated to release the adapter from the barrel to permit the adapter to be withdrawn into the barrel upon joint axial withdrawing movement of the plunger and adapter. In FIG. 5A, the fingers 82 are in a first position engageable with and between splines 80, inhibiting or preventing rotation of adapter 20 in a direction tending to release or unseal the adapter from the barrel end. Referring to FIGS. 5A and 5B, as the plunger advances toward the adapter, the rib 44 engages the tapered surfaces 84 of the fingers 82. Upon further axial movement of the plunger toward the adapter, the fingers 82 are displaced radially inwardly against their natural bias into a second position illustrated in FIG. 5B. In that second position, the projections 88 of fingers 82 are withdrawn by a substantial margin from between the splines 80, thereby releasing the adapter for rotation relative to the barrel end. As the fingers are displaced radially inwardly, the alignment surfaces of the adapter-engagement structure 24 contact the alignment surfaces of the plunger-engagement structure 24, automatically causing rotation of the plunger relative to the barrel and adapter to align and register the drive surfaces 36 and 78 of the plunger and adapter, respectively, in response to further axial movement of the plunger toward the adapter. As the plunger fully seats against the adapter, the ribs 44 engage in the slots 86, permitting the fingers 82 to spring back to a third position (FIG. 4C) intermediate the first and second positions. In the third position, the fingers 82 lie radially inwardly of the interior confines or edges of the splines 80 thereby enabling the adapter for rotation relative to the barrel without the fingers 82 engaging the splines 80. Also, the engagement of the ribs 44 in the slots 86 connect the plunger and adapter for joint axial movement, the ribs 44 and slots 86 forming parts of the respective engagement structures 22 and 24 on the adapter and plunger, respectively.

Figure 6:
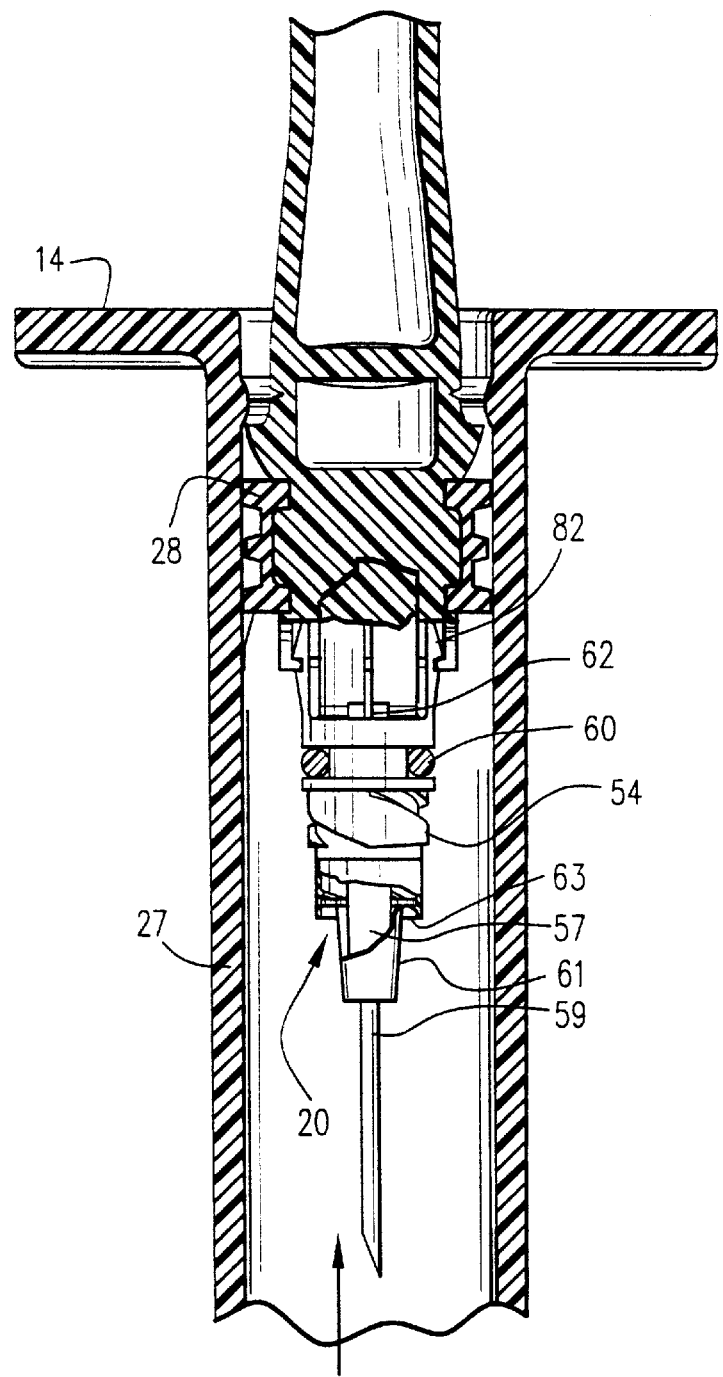
FIG. 6 is a fragmentary cross-sectional view illustrating the adapter withdrawn into the barrel.

With the plunger and adapter engaged as illustrated in FIG. 3, and the interengaging elements 80 and 82 disabled from preventing or inhibiting rotation of the adapter relative to the barrel, the plunger is rotated relative to the barrel. This causes the surfaces 36 to drive surfaces 78 of the adapter in a rotational direction, enabling release of the adapter from the barrel end. In a preferred embodiment, the rotation of the adapter relative to the barrel end unthreads the adapter from the barrel end, freeing it for axial movement. Once freed from the barrel (and with the rib 44 and the slots 86 of the adapter and plunger engagement structures 24 and 22, respectively, engaged with one another), the adapter and plunger are jointly withdrawn in an axial direction such that the adapter and needle carried by the plunger are located within the barrel as illustrated in FIG. 6. As in the above-mentioned patent, the plunger can be then broken away from the adapter-engagement structure at the distal end of the plunger and applied to the distal end of the barrel to seal that end whereby opposite ends of the barrel are sealed.

Figure 5C:
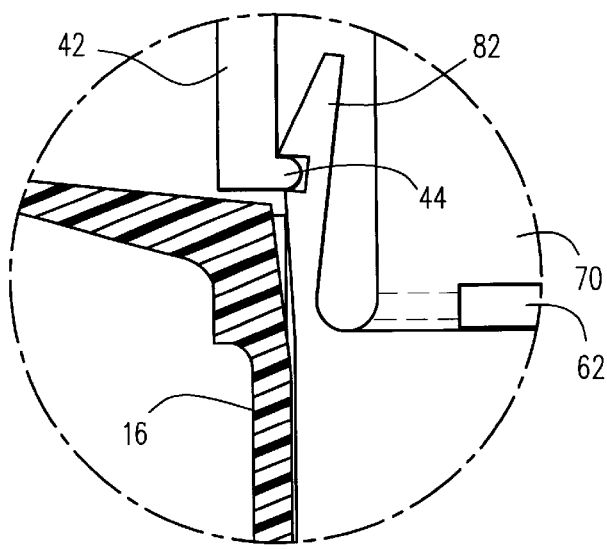
Figure 5D:
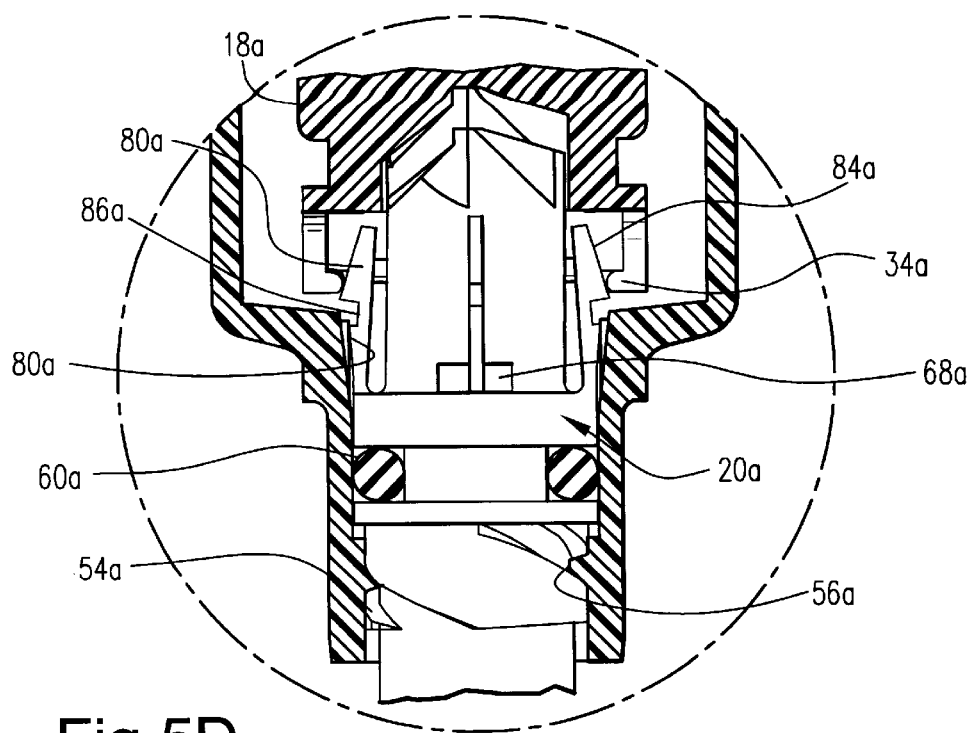
FIGS. 5D, 5E and 5F are views similar to FIGS. 5A—5C illustrating another embodiment of the present invention.
Figure 5E:
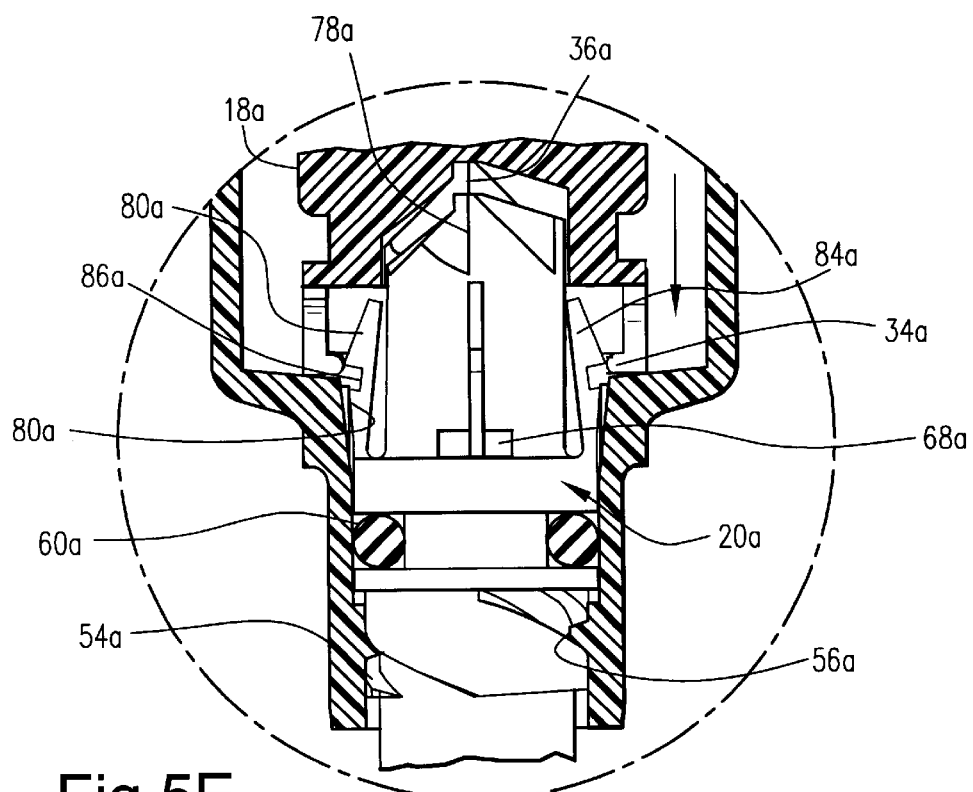
Figure 5F:
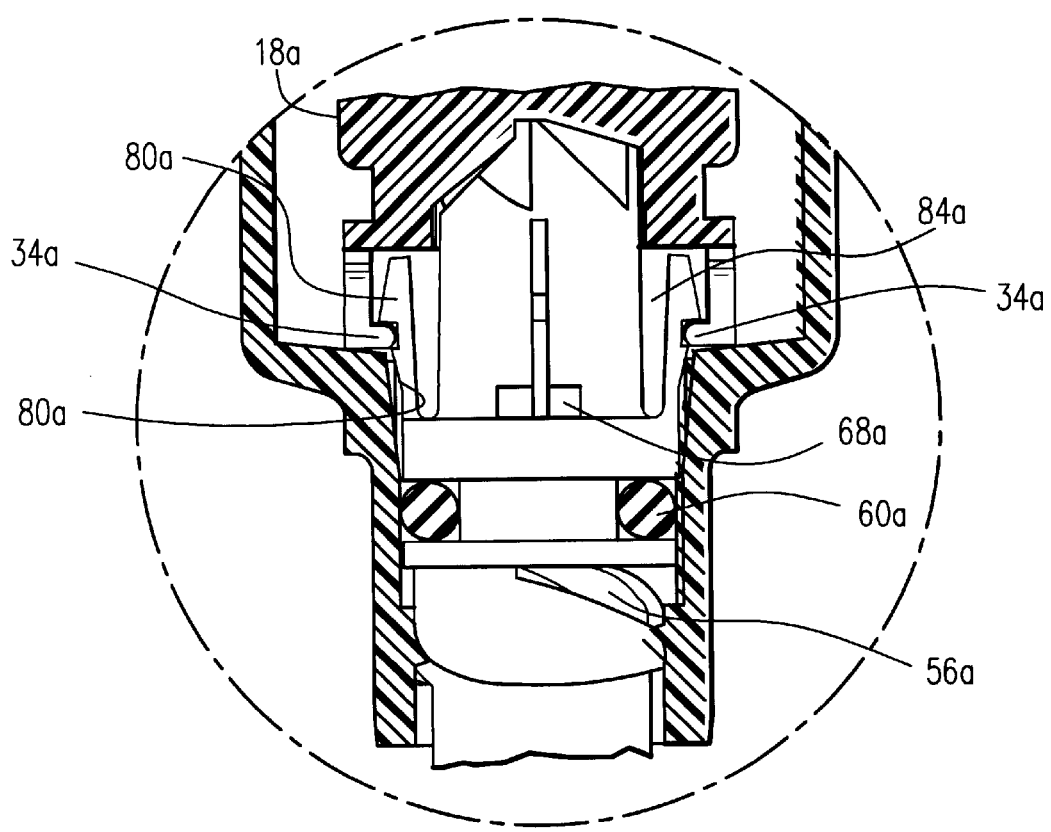

With the foregoing arrangement and particularly with respect to the finger/spline engagement and disengagement illustrated in FIGS. 5A—5C, it will be appreciated that axial movement of the plunger into a fully seated position vis-a-vis the adapter will cause ribs 44 to engage in slots 86 of fingers 82. This will lock the plunger and adapter to one another when the plunger is pushed to its fullest extent, i.e., in an axial direction toward the adapter. In certain situations, the foregoing is quite satisfactory. However, in other situations, for example, where the plunger is pressed home during expulsion of air to charge a medication vial prior to filling the syringe, the locking of the plunger and adapter to one another at that stage of the procedure would not permit the syringe to operate in its intended manner. To permit the plunger to move freely back and forth and particularly when the plunger fully engages the seated adapter, the recesses 86 in fingers 82 may be disposed closer to the needle end of the syringe barrel than as depicted in FIGS. 5A—5C. Adapter engagement structure and plunger engagement structure enabling the syringe for movement of the plunger relative to the barrel between a fully retracted position and a fully extended position in the barrel without locking the plunger and adapter to one another in the fully extended position are illustrated in FIGS. 5D—5F wherein like reference numerals are applied to like parts as in the preceding embodiment followed by the suffix "a." For example, in FIG. 5D, the recess 86a of finger 80a lies in partial registration with the margin of the barrel at the juncture of the distal end 16 and the radially outwardly flared end of the barrel. In this configuration, the rib 34a engages the tapered surface 84a of the finger to displace the finger radially inwardly beyond the radial inner edges of the splines 80a, thereby enabling the adapter for rotation. With the fingers displaced radially inwardly as in FIG. 5D, the drive surfaces 36a and 78a of the plunger and adapter, respectively, are at least partially engaged. Rotation of the plunger relative to the barrel will cause the adapter to unscrew from the front of the barrel. As best illustrated in FIG. 5F, and as the adapter backs out into the interior of the barrel, the openings 86a in the fingers 82a are exposed within the barrel and register radially with the rib 34a. Upon registration, the fingers are displaced radially outwardly under their natural outward bias to engage the rib 34a in the openings 86a. Further rotation of the plunger relative to the barrel completely unscrews the adapter from the barrel end, enabling the plunger and adapter to be withdrawn jointly, similarly as previously described.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A syringe comprising:
    an axially elongated barrel having a hollow interior;
    an adapter threadedly carried by said barrel adjacent a distal end thereof and releasable therefrom in response to rotation relative to and about the axis of the barrel to unthread the adapter from the barrel end, the adapter having a passage for providing fluid communication with the interior of the barrel;
    a plunger axially movable in said barrel between positions axially spaced from said adapter and engaging said adapter;
    adapter-engagement structure disposed adjacent a first end of the plunger and engageable with plunger engagement structure on the adapter for enabling rotation of the adapter relative to the barrel in response to relative rotation of the plunger and barrel to cause the adapter to unthread and part from the distal end of the barrel, said structures having engageable surfaces enabling withdrawal of said adapter, when unthreaded and parted from the distal end of the barrel, into the interior of the barrel upon joint axial movement of said plunger and said adapter in a direction away from the distal end of the barrel; and
    a stop carried by one of said adapter and the distal end of the barrel and a catch carried by another of said adapter and the distal end of the barrel engageable with said stop in a first position thereof to at least inhibit relative rotational movement of said adapter and said distal end of the barrel in a direction tending to cause the adapter to part from the distal end of the barrel, said catch being movable to a second position to release the adapter and the distal end of the barrel for relative rotational movement enabling the adapter to unthread and part from the distal end of the barrel in response to relative rotation of the adapter and the barrel.

2. A syringe according to claim 1 wherein said catch is movable from said first position toward said second position in a direction generally normal to said axis.

3. A syringe according to claim 2 wherein said stop includes a generally radially inward projection carried by said barrel, said catch including a radially outward projection carried by said adapter.

4. A syringe according to claim 3 wherein said catch is flexible and maintains a bias into said first position.

5. A syringe according to claim 1 including an element carried by said plunger and engageable with said catch to move said catch from said first position toward said second position.

6. A syringe according to claim 5 wherein said catch includes a tapered surface engageable by said element for moving said catch from said first position into said second position.

7. A syringe according to claim 5 wherein said element comprises the engageable surfaces of said adapter engagement structure and said catch comprises in part the engageable surfaces of said plunger engagement structure carried by said adapter.

8. A syringe according to claim 7 wherein said element is engageable with said catch to move said catch from said first position into a third position, said catch being movable from said third position into said second position, in response to engagement of said engageable surfaces.

9. A syringe according to claim 8 wherein said engageable surfaces cooperate with one another to preclude movement of said catch from said second position into said first position after said catch has been moved from said third position into said second position thereby preventing said catch and said stop from inhibiting relative rotational movement of said adapter and said distal end of the barrel and enabling the joint axial movement of the plunger and the adapter upon rotation of the adapter relative to the barrel to part the adapter from the distal end of the barrel.

10. A syringe according to claim 1 wherein engagement of said engagement surfaces disables movement of the catch from said second position toward said first position enabling relative rotation of the adapter and the distal end of the barrel to release the adapter from the distal end of the barrel.

11. A syringe according to claim 1 wherein said catch is movable from said first position toward said second position in response to engagement of said plunger and said adapter with one another.

12. A syringe according to claim 1 wherein said catch is movable from said first position toward said second position in response to axial movement of said plunger toward said adapter.

13. A syringe according to claim 1 wherein said engageable surfaces are located to enable engagement thereof in response to a movement of said adapter in a direction away from the distal end of the barrel.

14. A syringe according to claim 1 wherein said adapter is screwthreaded into the distal end of the barrel, said engageable surfaces being located to enable engagement thereof in response to joint rotation of the plunger and adapter, causing the adapter to at least partially unthread from the end of the barrel and move axially in a direction away from the distal end of the barrel.

15. A syringe comprising:

an axially elongated barrel having a hollow interior;

an adapter carried by said barrel adjacent a distal end thereof and removable therefrom in response to rotation relative to and about the axis of the barrel, the adapter having a passage for providing fluid communication with the interior of the barrel;

a plunger axially movable in said barrel between positions axially spaced from said adapter and engaging said adapter;

an adapter-engagement structure disposed adjacent a first end of the plunger and engageable with mating engagement structure on the adapter for enabling rotation of the adapter and distal end of the barrel relative to one another to cause the adapter to part from the distal end of the barrel in response to said relative rotation;

means cooperable between the adapter and the barrel for preventing relative rotation of the adapter and the distal end of the barrel;

connective surfaces engageable between said plunger and adapter enabling withdrawal of said adapter, when parted from the distal end of the barrel, into the interior of the barrel upon joint axial movement of said plunger and said adapter in a direction away from the distal end of the barrel; and means cooperable between the plunger and the adapter for disabling said preventing means thereby enabling relative rotation of the adapter and the distal end of the barrel followed by withdrawal of the adapter, when parted from the distal end of the barrel, into the interior of the barrel.

16. A syringe according to claim 15 wherein said preventing means includes a plurality of splines carried by one of said adapter and said barrel end and a projection carried by another of said adapter and said barrel end and engageable with said splines.

17. A syringe according to claim 15 wherein said disabling means includes at least one of said connective surfaces.

18. A syringe comprising:

an axially elongated barrel having a hollow interior;

an adapter carried by said barrel adjacent a distal end thereof and removable therefrom in response to rotation relative to and about the axis of the barrel, the adapter having a passage for providing fluid communication with the interior of the barrel;

a plunger axially movable in said barrel between positions axially spaced from said adapter and engaging said adapter;

an adapter-engagement structure disposed adjacent a first end of the plunger and engageable with mating engagement structure on the adapter for enabling rotation of the adapter and distal end of the barrel relative to one another to cause the adapter to part from the distal end of the barrel in response to said relative rotation;

first elements interengageable between the adapter and the barrel for preventing relative rotation of the adapter and the distal end of the barrel;

connective surfaces engageable between said plunger and adapter enabling withdrawal of said adapter, when parted from the distal end of the barrel, into the interior of the barrel upon joint axial movement of said plunger and said adapter in a direction away from the distal end of the barrel; and elements cooperable between the plunger and the adapter to disable said interengageable elements from preventing relative rotation of the adapter and the distal end of the barrel thereby enabling relative rotation of the adapter and the distal end of the barrel followed by withdrawal of the adapter, when parted from the distal end of the barrel, into the interior of the barrel.

19. A syringe according to claim 18 wherein said interengageable elements includes a plurality of splines carried by one of said adapter and said barrel end and a projection carried by another of said adapter and said barrel end and engageable with said splines.

20. A syringe according to claim 18 wherein said disabling elements includes at least one of said connective surfaces.

21. A syringe according to claim 18 wherein said disabling elements are responsive to axial movement of the adapter and plunger relative to one another to disable said interengageable elements from preventing relative rotation of the adapter and the distal end of the barrel.

22. A syringe according to claim 15 wherein said disabling means cooperate between the plunger and the adapter to enable relative rotation between the adapter and the barrel end before said connective surfaces of said plunger and said adapter are engaged to withdraw the adapter away from the distal barrel end.

23. A syringe according to claim 18 wherein said disabling elements cooperate between the plunger and adapter to enable relative rotation between the adapter and the barrel end before said connective surfaces of said plunger and adapter are engaged to withdraw the adapter away from the distal barrel end.

* * * * *